United States Patent
Ribnick et al.

(10) Patent No.: US 9,841,383 B2
(45) Date of Patent: Dec. 12, 2017

(54) MULTISCALE UNIFORMITY ANALYSIS OF A MATERIAL

(71) Applicant: 3M INNOVATIVE PROPERTIES COMPANY, St. Paul, MN (US)

(72) Inventors: Evan J. Ribnick, St. Louis Park, MN (US); John A. Ramthun, Hudson, WI (US); David D. Miller, North St. Paul, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 23 days.

(21) Appl. No.: 15/032,735

(22) PCT Filed: Oct. 16, 2014

(86) PCT No.: PCT/US2014/060898
§ 371 (c)(1),
(2) Date: Apr. 28, 2016

(87) PCT Pub. No.: WO2015/065726
PCT Pub. Date: May 7, 2015

(65) Prior Publication Data
US 2016/0282279 A1    Sep. 29, 2016

Related U.S. Application Data

(60) Provisional application No. 61/898,304, filed on Oct. 31, 2013.

(51) Int. Cl.
*G06K 9/00*    (2006.01)
*G01N 21/898*    (2006.01)
(Continued)

(52) U.S. Cl.
CPC ..... *G01N 21/8983* (2013.01); *G01N 21/8422* (2013.01); *G01N 21/8851* (2013.01);
(Continued)

(58) Field of Classification Search
CPC .......... G01N 21/8422; G01N 21/8983; G01N 2021/8427; G01N 21/8851;
(Continued)

(56) References Cited

U.S. PATENT DOCUMENTS 5,774,574 A    6/1998   Hoki
6,239,554 B1   5/2001   Tessadro
(Continued)

FOREIGN PATENT DOCUMENTS

JP    11-94767      4/1999
JP    2001-266122   9/2001
(Continued)

OTHER PUBLICATIONS

International Search Report for PCT International Application No. PCT/US2014/060898 dated Jan. 27, 2015, 4 pages.
(Continued)

*Primary Examiner* — Gregory F Cunningham
(74) *Attorney, Agent, or Firm* — James A. Baker

(57) ABSTRACT

A method for characterizing the uniformity of a material includes selecting a set of size scales at which to measure uniformity within an area of interest in an image of the material; suppressing features in the image smaller than a selected size scale of interest within the set of size scales; dividing the image into patches equal to the size scale of interest; and calculating a uniformity value within each patch.

27 Claims, 6 Drawing Sheets

(51) Int. Cl.
*G01N 21/84* (2006.01)
*G01N 21/89* (2006.01)
*G01N 21/88* (2006.01)
*G06T 3/40* (2006.01)
*G06T 5/20* (2006.01)
*G06T 7/00* (2017.01)
*G06T 7/11* (2017.01)
*G06T 7/44* (2017.01)

(52) U.S. Cl.
CPC .......... *G01N 21/8915* (2013.01); *G06T 3/40* (2013.01); *G06T 5/20* (2013.01); *G06T 7/0004* (2013.01); *G06T 7/11* (2017.01); *G06T 7/44* (2017.01); *G01N 2021/8427* (2013.01); *G01N 2021/8917* (2013.01); *G01N 2201/12* (2013.01); *G06T 2207/20016* (2013.01); *G06T 2207/20021* (2013.01); *G06T 2207/30124* (2013.01)

(58) Field of Classification Search
CPC ....... G01N 2201/12; G01N 2021/8917; G01N 21/8915; G06T 7/44; G06T 2207/20016; G06T 2207/30124; G06T 7/0004; G06T 5/20; G06T 3/40; G06T 2207/20021; G06T 7/11
USPC ........................................................ 382/111
See application file for complete search history.

(56) References Cited

U.S. PATENT DOCUMENTS

| | | | |
|---|---|---|---|
| 6,301,373 | B1 | 10/2001 | Bernie |
| 2005/0004956 | A1 | 1/2005 | Pourdeyhimi |
| 2009/0051907 | A1* | 2/2009 | Li .......................... G02F 1/1309 356/218 |
| 2009/0310864 | A1 | 12/2009 | Takagi et al. |
| 2011/0157584 | A1 | 6/2011 | Lin |
| 2012/0327214 | A1* | 12/2012 | McEntyre ............ H04N 17/002 348/86 |
| 2013/0033620 | A1 | 2/2013 | Polidor |
| 2013/0083324 | A1 | 4/2013 | Wilhelm |

FOREIGN PATENT DOCUMENTS

| | | |
|---|---|---|
| JP | 2002-228594 | 8/2002 |
| TW | 200951878 | 12/2009 |
| WO | 2012115819 | 8/2012 |
| WO | WO 2013-015699 | 1/2013 |
| WO | WO 2013-051786 | 4/2013 |

OTHER PUBLICATIONS

Kenneth Ivan Laws A: "Textured image segmentation", Uscript Report 940, Universtiy of Southern California 1980, US, val. 84, Jan. 1, 1980 (Jan. 1, 1980), pp. 1-195, XP008184787, Retrieved from the Internet: URL:http://www.dlic.mil/docs/citations/ADA083283.

Bresee R R et al: "Characterizing Nonwoven Web Structure Using Image Analysis Techniques", Tappi Journal, Technical Association of the Pulp & Paper Industry. Atlanta, US, vol. 80, No. 7, Jul. 1, 1997 (Jul. 1, 1997), pp. 133-138, XP000751858, ISSN: 0734-1415.

Nickolay B et al: "Automatisierte Visuelle Inspektion Auf Basis Einer Hierarchischen Bildaufloesung", Zvvf Zeitschrift Fur Wirtschaftliche Fertigung Undautomatisierung, Carl Hanser Verlag. Munchen, DE, vol. 87, No. 1, Jan. 1, 1992 (Jan. 1, 1992), pp. 34-37, XP000271912, ISSN: 0947-0085.

Nickolay B: "Uberwacht lernendes Bildauswertungssystem zur Erkennung von Oberflachenfehlern", Aug. 1, 1990 (Aug. 1, 1990), Carl Hanser Verlag Munchen, Berlin, ISBN: 3-446-16176-7, val. 1, pp. 32-39-116-137.

Nickolay B et al: "Texturanalyse mittels Co-OccuranceMatrizen zur autmatisierten Oberflaechenpruefung", Jan. 1, 1988 (Jan. 1, 1988), Conference Info: ZWF83 (1988), Carl Hanser Verlag, Miinchen 1988, DE, pp. 90 94, XP008184789.

* cited by examiner

MULTISCALE UNIFORMITY ANALYSIS OF A MATERIAL

CROSS REFERENCE TO RELATED APPLICATIONS

This application is a national stage filing under 35 U.S.C. 371 of PCT/US2014/060898, filed Oct. 16, 2014, which claims the benefit of U.S. Application No. 61/898,304 filed Oct. 31, 2013, the disclosure of which is incorporated by reference in its/their entirety herein.

BACKGROUND

A selected physical attribute of a material can be analyzed to determine the uniformity of the material, which in turn can provide useful information regarding the appearance and functionality of the material in a particular product application. Methods for analyzing and determining uniformity have relied on pictorial standards and the judgment of human experts, but such qualitative methods lack precision and cannot be utilized in real-time as a product is manufactured.

Optical methods have been used to measure physical properties of materials in real-time. However, rapidly evaluating the overall uniformity of a material based on these measurements has proven to be difficult, as some non-uniformities are present at small size scales, while others are apparent only at larger size scales.

SUMMARY

Listing of Embodiments

A. A method for characterizing the uniformity of a material, including selecting a set of size scales at which to measure uniformity within an area of interest in an image of the material; suppressing features in the image smaller than a selected size scale of interest within the set of size scales; dividing the image into patches equal to the size scale of interest; and calculating a uniformity value within each patch.

B. The method of embodiment A, wherein suppressing the features comprises processing the image with a low-pass filter.

C. The method of embodiments A-B, wherein the low pass filter comprises a box filter with a cutoff frequency equal to a predetermined fraction of the size scale of interest.

D. The method of embodiments A-B, wherein the low-pass filter comprises a two-dimensional Gaussian kernel.

E. The method of any of embodiments A-D, wherein the uniformity value is calculated by determining at least one of a standard deviation, an inter-quartile range (IQR), a median absolute deviation, or an information entropy of a selected characteristic of the patch.

F. The method of embodiment E, wherein the selected characteristic of the patch comprises an intensity of light transmitted through the patch or reflected off a surface of the material comprising the patch.

G. The method of embodiment E, wherein the uniformity value is calculated by determining the inter-quartile range (IQR) of an intensity of the light transmitted through the patch.

H. The method of any of embodiments A-G, further comprising scaling the area of interest to a predetermined size prior to removing the features.

I. The method of any of embodiments A-H, further comprising calibrating the area of interest prior to removing the features.

J. The method of any of embodiments A-G, further comprising aggregating the uniformity values of the patches to determine a uniformity value for the area of interest.

K. The method of any of embodiments A-J, further comprising aggregating the uniformity values of a selected array of patches within the area of interest to provide an uniformity value for the area of interest.

L. The method of any of embodiments A-L, wherein the material is selected from wovens, non-wovens, paper, coatings, polymeric films and combinations thereof.

M. The method of embodiment L, wherein the material is a non-woven.

N. The method of any of embodiments A-M, wherein the image is obtained by transmitting light through or reflecting light off a surface of the material comprising the area of interest.

O. The method of embodiment N, wherein the image is obtained by transmitting light through the material to an optical receiving device.

P. A method for characterizing the uniformity of a material, including obtaining an image of an area of interest of the material by transmitting light through the material to an optical receiving device; selecting a graduated set of size scales at which to measure uniformity within the area of interest; convolving a low-pass filter with the image to suppress features in the image smaller than a selected size scale of interest within the graduated set of size scales; dividing the image into patches equal to the size scale of interest, wherein the patches each comprise an array of pixels; and determining a standard deviation of the light intensity in the pixels in the array to calculate a uniformity value within each patch.

Q. The method of embodiment P, wherein the low pass filter comprises a box filter with a width equal to a predetermined fraction of the pixels within the array.

R. The method of embodiment Q, wherein the low-pass filter replaces a selected pixel in the array with a weighted average of the light intensities of the pixels surrounding the selected pixel, and wherein the weighted average is determined by a two-dimensional Gaussian kernel.

S. The method of any of embodiments P-R, further comprising determining an ideal pixel size for analyzing a selected non-uniformity, and scaling the area of interest to the ideal pixel size prior to removing the features.

T. The method of any of embodiments P-S, further comprising calibrating the area of interest prior to removing the features.

U. The method of any of embodiments P-T, further comprising aggregating the uniformity values of the patches to determine a uniformity value for the area of interest.

V. The method of any of embodiments P-U, further comprising aggregating the uniformity values of a selected array of patches within the area of interest to provide an uniformity value for the area of interest.

W. The method of any of embodiments P-V, wherein the material is selected from wovens, non-wovens, paper, coatings, polymeric films and combinations thereof.

X. The method of embodiment W, wherein the material is a non-woven.

Y. An apparatus, comprising: at least one light source illuminating a web of a material; a camera that captures light transmitted through or reflected from an area of interest on the material to generate an image of the area of interest; and a processor which, in response to an input of a set of size scales at which to measure uniformity within the area of interest: convolves a low-pass filter with the image to suppress features in the image smaller than a selected size scale of interest within the set of size scales; divides the image into patches equal to the size scale of interest, wherein the patches each comprise an array of pixels; and calculates a uniformity value within each patch.

Z. The apparatus of embodiment Y, wherein the processor calculates the uniformity value by determining at least one of a standard deviation, an inter-quartile range (IQR), a median absolute deviation, or an information entropy of a light intensity in the pixels in the array.

AA. The apparatus of any of embodiments Y-Z, wherein the processor calculates the uniformity value by determining the inter-quartile range (IQR).

BB. The apparatus of any of embodiments Y-AA, wherein the low pass filter comprises a box filter with a width equal to a predetermined fraction of the pixels within the array.

CC. The apparatus of any of embodiments Y-BB, wherein the low-pass filter replaces a selected pixel in the array with a weighted average of the light intensities of the pixels surrounding the selected pixel, and wherein the weighted average is determined by a two-dimensional Gaussian kernel.

DD. The apparatus of any of embodiments Y-CC, wherein the processor further determines an ideal pixel size for analyzing a selected non-uniformity in the material, and scales the area of interest to the ideal pixel size prior to removing the features.

EE. The apparatus of any of embodiments Y-DD, wherein the processor calibrates the area of interest prior to removing the features.

FF. The apparatus of any of embodiments Y-EE, wherein the processor aggregates the uniformity values of the patches to determine a uniformity value for the area of interest.

GG. The apparatus of any of embodiments Y-FF, wherein the processor aggregates the uniformity values of a selected array of patches within the area of interest to provide a uniformity value for the area of interest.

HH. The apparatus of any of embodiments Y-GG, wherein the material is selected from non-wovens and polymeric films.

II. The apparatus of embodiment HH, wherein the material is a non-woven.

JJ. The apparatus of any of embodiments Y-HH, wherein the camera captures light transmitted through the area of interest.

KK. The apparatus of embodiment JJ, wherein only scattered light is captured by the camera to form the image.

LL. The apparatus of embodiment KK, wherein a dark stripe is placed across the light source, and the camera is aimed directly at the dark stripe.

MM. A method for inspecting web material in real time and computing a level of uniformity of an area of interest in a surface of the web material as the web material is manufactured, comprising: obtaining an image of the area of interest by transmitting light through the material to an optical receiving device; selecting a set of size scales at which to measure uniformity within the area of interest; convolving a low-pass filter with the image to suppress features in the image smaller than a selected size scale of interest within the set of size scales; dividing the image into patches equal to the size scale of interest, wherein the patches each comprise an array of pixels; and calculating a uniformity value within each patch.

NN. The method of embodiment MM, wherein the uniformity value is calculated by determining the inter-quartile range (IQR) of the light intensity in the pixels in the array.

OO. The method of any of embodiments MM-NN, wherein the low pass filter comprises a box filter with a width equal to a predetermined fraction of the pixels within the array.

PP. The method of any of embodiments MM-OO, wherein the low-pass filter replaces a selected pixel in the array with a weighted average of the light intensities of the pixels surrounding the selected pixel, and wherein the weighted average is determined by a two-dimensional Gaussian kernel.

QQ. The method of any of embodiments MM-PP, further comprising determining an ideal pixel size for analyzing a selected non-uniformity, and scaling the area of interest to the ideal pixel size prior to removing the features.

RR. The method of any of embodiments MM-QQ, further comprising calibrating the area of interest prior to removing the features.

SS. The method of any of embodiments MM-RR, further comprising aggregating the uniformity values of the patches to determine a uniformity value for the area of interest.

TT. The method of any of embodiments MM-SS, further comprising aggregating the uniformity values of a selected array of patches within the area of interest to provide an uniformity value for the area of interest.

UU. The method of any of embodiments MM-TT, wherein the material is a non-woven.

VV. An online computerized inspection system for inspecting web material in real time, the system comprising: at least one light source illuminating a web of a material; a camera that captures light transmitted through or reflected from an area of interest on the material to generate an image of the area of interest; and a computer executing software to characterize the uniformity of the material in the area of interest, wherein the computer comprises a processor which, in response to an input of a set of size scales at which to measure uniformity within the area of interest: convolves a low-pass filter with the image to suppress features in the image smaller than a selected size scale of interest within the set of size scales; divides the image into patches equal to the size scale of interest, wherein the patches each comprise an array of pixels; and calculates a uniformity value within each patch.

WW. The system of embodiment VV, further comprising a memory to store a web inspection model, wherein the computer executes software to compare the uniformity in the area of interest to the model and compute a severity of a non-uniformity defect in the material.

XX. The system of any of embodiments VV-WW, further comprising a user interface to output the severity of the defect to a user.

YY. The system of any of embodiments VV-XX, wherein the material is a non-woven.

ZZ. A non-transitory computer readable medium comprising software instructions to cause a computer processor to: receive, with an online computerized inspection system, an image of one or more areas of interest on a surface of a web material during the manufacture thereof; select a set of size scales at which to measure uniformity within the area of interest; convolve a low-pass filter with the image to suppress features in the image smaller than a selected size scale of interest within the set of size scales; divide the image into patches equal to the size scale of interest, wherein the patches each comprise an array of pixels; and calculate a uniformity value within each patch.

AAA. The computer readable medium of embodiment ZZ, wherein the uniformity value is calculated by determining the inter-quartile range (IQR) of the light intensity in the pixels in the array.

BBB. The computer readable medium of any of embodiments ZZ-AAA, wherein the low pass filter comprises a box filter with a width equal to a predetermined fraction of the pixels within the array.

CCC. The computer readable medium of any of embodiments ZZ-BBB, wherein the low-pass filter replaces a selected pixel in the array with a weighted average of the light intensities of the pixels surrounding the selected pixel, and wherein the weighted average is determined by a two-dimensional Gaussian kernel.

DDD. The computer readable medium of any of embodiments ZZ-CCC, wherein the processor further determines an ideal pixel size for analyzing a selected non-uniformity, and scaling the area of interest to the ideal pixel size prior to removing the features.

EEE. The computer readable medium of any of embodiments ZZ-DDD, wherein the processor calibrates the area of interest prior to removing the features.

FFF. The computer readable medium of any of embodiments ZZ-EEE, wherein the processor aggregates the uniformity values of the patches to determine a uniformity value for the area of interest.

GGG. The computer readable medium of any of embodiments ZZ-FFF, wherein the processor aggregates the uniformity values of a selected array of patches within the area of interest to provide a uniformity value for the area of interest.

HHH. The computer readable medium of any of embodiments ZZ-GGG, wherein the material is a non-woven.

The terms "about" or "approximately" with reference to a numerical value, property, or characteristic, means+/−five percent of the numerical value, property, characteristic, but also expressly includes any narrow range within the +/−five percent of the numerical value or property or characteristic as well as the exact numerical value. For example, a temperature of "about" 100° C. refers to a temperature from 95° C. to 105° C., inclusive, but also expressly includes any narrower range of temperature or even a single temperature within that range, including, for example, a temperature of exactly 100° C.

The term "substantially" with reference to a property or characteristic means that the property or characteristic is exhibited to within 98% of that property or characteristic, but also expressly includes any narrow range within the two percent of the property or characteristic, as well as the exact value of the property or characteristic. For example, a substrate that is "substantially" transparent refers to a substrate that transmits 98-100%, inclusive, of the incident light.

The details of one or more embodiments of the invention are set forth in the accompanying drawings and the description below. Other features, objects, and advantages of the invention will be apparent from the description and drawings, and from the claims.

DETAILED DESCRIPTION

Depending on the needs of a particular application, the uniformity of a material at some size scales might be deemed as more important than at others. For example, in applications where the material is to be converted into small pieces, a non-uniformity at a size scale much larger than these pieces may not have any cosmetic impact, since it will not be visible within the extent of a single small piece. On the other hand, larger-scale non-uniformities may cause differences in functional properties between samples.

In general, the present disclosure is directed to an inspection technique to characterize the uniformity of an area of interest in a sample of a material. Images of the area of interest are captured using an optical inspection system and processed using image processing algorithms to determine the uniformity (or conversely, non-uniformity) over a set of size scales (for example, from 1 mm to 10 cm in increments of 1 mm) selected to evaluate a particular appearance or performance metric of the material.

At each size scale of interest within the set of size scales, the captured image is processed to remove image features significantly smaller than the size scale of interest. The image is then divided into areas equal to the size scale of interest, referred to herein as patches, and the uniformity of each patch is evaluated using a metric selected to provide a quantitative and repeatable measurement of the overall uniformity for that patch size.

The measurements obtained for each patch may then be utilized for further analysis of the area of interest or of the material. For example, the uniformity measurements for all or a selected group of patches within the area of interest may be aggregated to calculate a single uniformity value for the area of interest. The calculated uniformity values may be utilized in a wide variety of ways. In one non-limiting example, the uniformity values may be monitored in real-time during manufacturing operations to assess the appearance of the material or the functionality of the product of which the material is a part.

Figure 1:
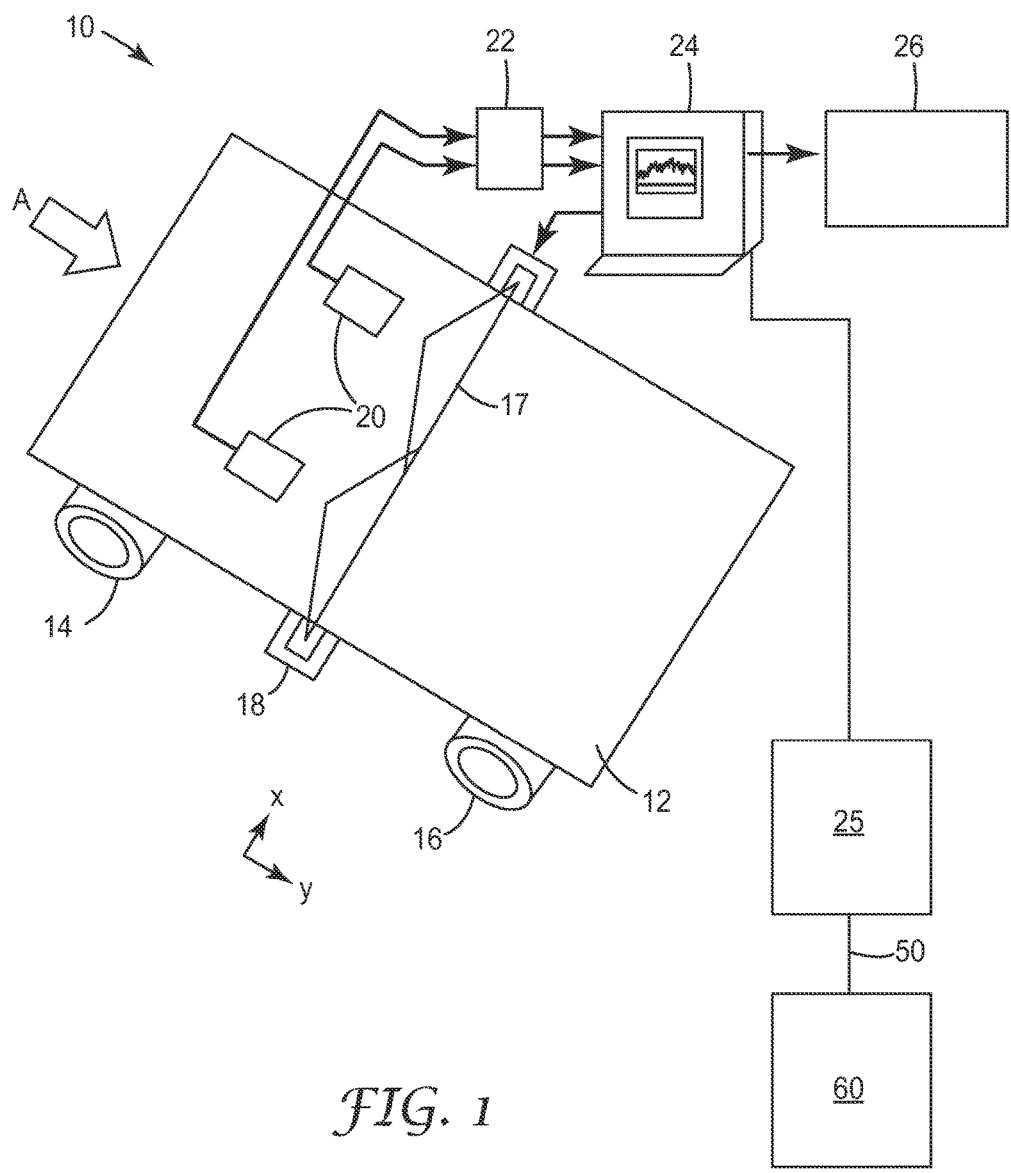
FIG. 1 is a schematic overhead perspective view of an embodiment of an online optical data acquisition system for characterizing the uniformity of a web material using the methods described in this disclosure.

FIG. 1 depicts an embodiment, which is not intended to be limiting, of an online optical data acquisition system suitable for characterizing the uniformity of a web material using the methods described in this disclosure. It should be emphasized the system 10 is only an example, and the image processing algorithms described herein are largely independent of the system used to capture the images of the web of material. In FIG. 1, the data acquisition system 10 includes a web of material 12 moving in the direction of arrow A between rollers 14, 16. The web of material 12 may be selected from, for example, wovens, non-wovens, paper, polymeric films, or a coating layer applied on a substrate. A light source 18 emits light through the web material 12, and illuminates an area of interest 17 in the web material 12. The light source 18 may image the area of interest 17 using any suitable part of the spectrum, including wavelengths outside the visible range such as, for example, infrared or ultraviolet. After passing through the material 12, an image of the area of interest 17 is captured by an array of cameras 20, such as, for example, line-scan cameras. However, any camera or other type of detector may be used that is suitable to capture an image of the area of interest 17. The image of the area of interest is transmitted to a data acquisition module 22, and then to a computer 24. The computer 24 includes a processor than can process in real-time the images obtained by the array of cameras 20 as the web material 12 is manufactured, coated or otherwise processed. Results from the processing of the image of the area of interest 17 can be displayed for a user on the display 26.

In FIG. 1, the web material 12 is illuminated from behind, while the cameras 20 image from above the web material 12, so the light passes through the web material 12 before being imaged by the camera 20. This type of backlight configuration, which is referred to herein as imaging in transmission mode, is useful for some applications, since it can accentuate non-uniformities in web thickness or openness. Web materials that can be analyzed in transmission mode include, but are not limited to, nonwovens or transparent or translucent polymeric films.

For applications where the web material is more dense or sheet-like, a top-light configuration may be used (not shown in FIG. 1), wherein the light source and the camera are on the same side of the web material. This type of top-light configuration is referred to herein as imaging in reflection mode, wherein the camera images light that is reflected off a surface of the web material. Imaging in reflection mode may be more suitable for analysis of woven materials or materials or coatings that do not readily transmit the wavelength of light emitted by the light source.

Figure 2:
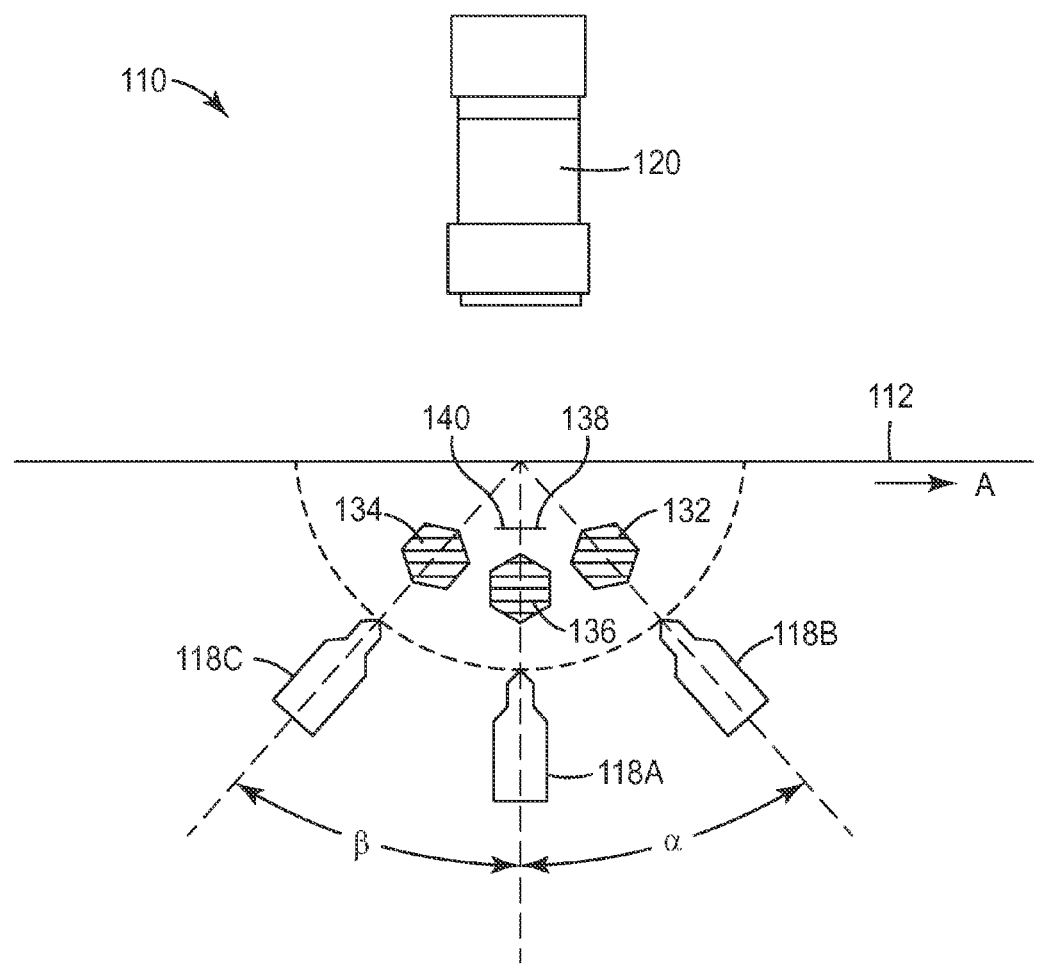
FIG. 2 is a schematic side view of an optical data acquisition system operating in transmission mode.

FIG. 2 is a side view of an optical illumination system 110 suitable for evaluating the uniformity of a web of material 112 which is typically of indefinite length and moving in a direction A. The illumination system 110 includes at least two, or in some embodiments, three light sources, and in some embodiments at least some of the light sources may be collimated. A direct source 118A emits light in the direction of a camera 120. Far dark field light sources 118B and 118C emit light at an angle ($\alpha+\beta$, respectively) to the imaging camera 120. Most conveniently, the direct light source 118A is positioned to illuminate in a direction normal to a plane of the moving web of material 112. In some embodiments, the light source 118A source is a fiber light line or as a fluorescent lamp illuminating a strip across an entire width of the web of material 112. While it is convenient to orient this strip parallel to the cross web direction, this is not believed to be essential.

The dark field light sources 118B and 118C also can be conveniently provided as fiber light lines, although in some embodiments a laser source or other source may be employed. The dark field sources 118B and 118C conveniently illuminate a strip across the entire width of the web of material 112, oriented along the cross web direction. However, in some embodiments, they are mounted at an angle to the direction normal to the plane of the web of material 112

Figure 2A:
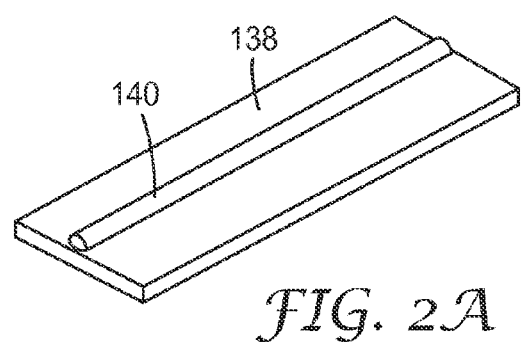
FIG. 2A shows a dark stripe above a diffuser.

In some embodiments, lenses can be used to focus the light emerging from the direct light source 118A and the two dark field sources 118B, 118C. For example, when fiber light lines are used as the sources, cylindrical lenses oriented parallel to the fiber light lines may be used. The cylindrical lenses 132 and 134 preferably focus the light from far dark field sources 118B and 118C onto the underside of the web 112 on a line directly under the camera 120. The cylindrical lens 136 that focuses light from direct light source 118A can have the same focal length as cylindrical lenses 132 and 134, but the light from the direct source 11A is directed onto a diffuser 138. In one embodiment, the diffuser 138 is a diffuser film. A dark line on the diffuser film, or another solid object, for example a taut cable or narrow piece of metal 140 mounted just above (or on) the diffuser 138, can provide the dark stripe as shown in FIG. 2A. In some embodiments, the dark stripe 140 is preferably very dark, which can, for example, be conveniently employed by using a cable that has carbon black colored insulation.

Figure 3:
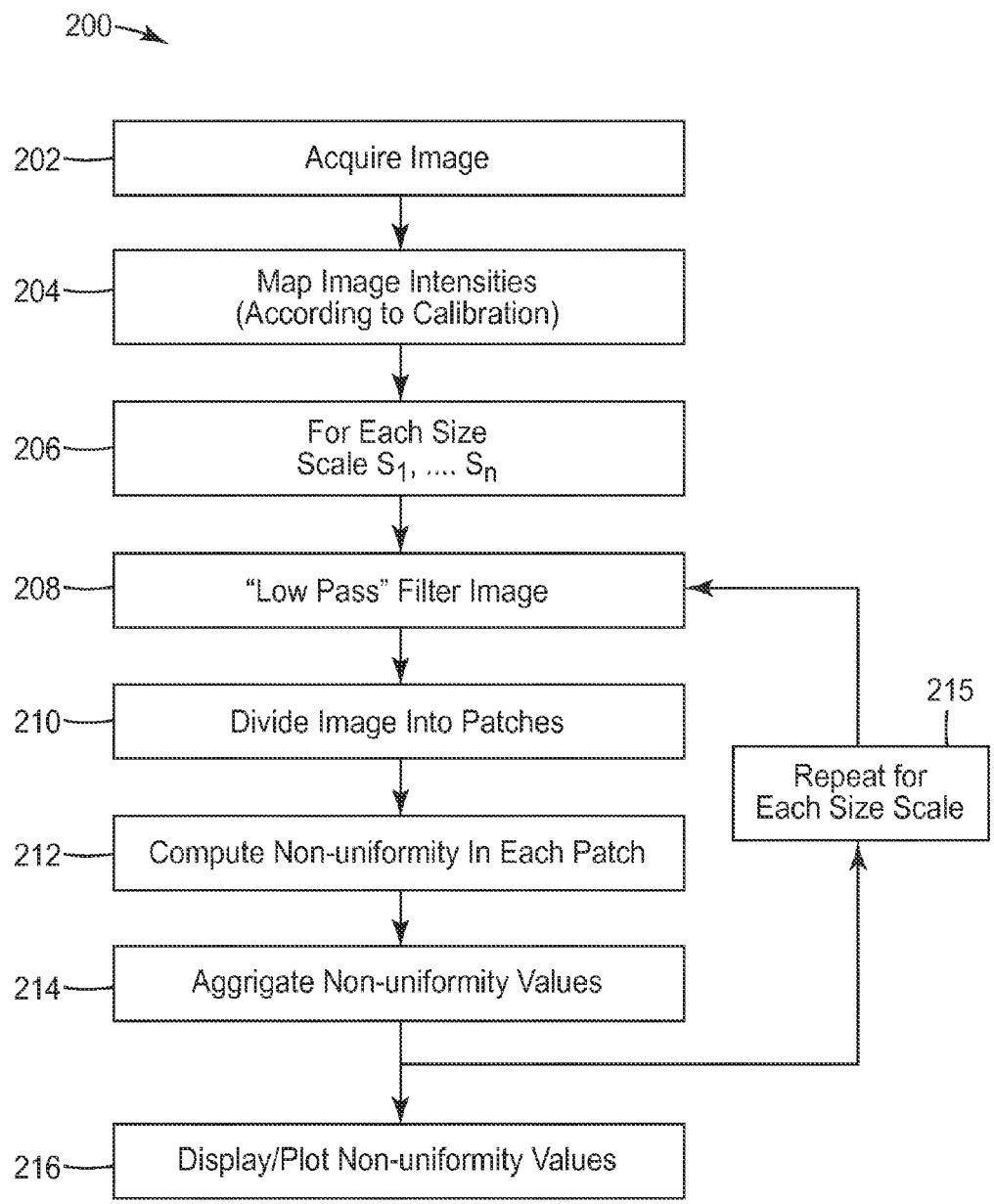
FIG. 3 is a flowchart illustrating an image processing algorithm suitable for characterizing the non-uniformity of a material using an optical data acquisition system.

Referring to FIG. 3, in an image processing procedure 200 may be applied to an image of the area of interest of the material captured by the camera 20 and acquired by the acquisition module 22 (FIG. 1) to characterize the uniformity of the area of interest 17 of the web material 12.

In some embodiments, after the image is acquired by the camera in step 202, prior to application of further image processing algorithms, the image may optionally be calibrated in step 204, and the image intensities mapped according to the calibration. The images obtained by the camera in FIG. 1 are intensity values in pixellated form, and in some embodiments it is preferred that these intensity values be constant for differing levels of optical transmission. Since the uniformity values depend on measured intensities, maintaining stable and repeatable mappings from transmission to pixel intensity can provide enhanced accuracy over time on a given inspection system and between different inspection systems.

Figure 4:
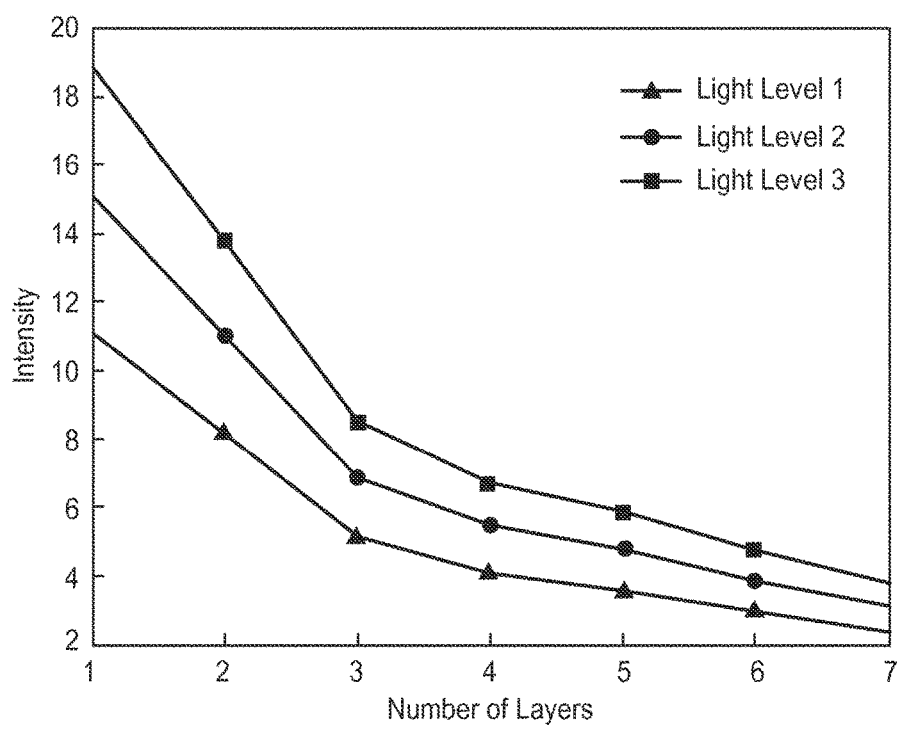
FIG. 4 is a plot of intensity vs. number of layers for three different light levels in an embodiment of an optical data acquisition system.

For example, for a dark-stripe illumination inspection system such as described in FIG. 2, in one embodiment an intensity calibration can be based on acquiring an image of a calibration pattern. For example, a diffuser film standard can be made by stacking together combinations of different thicknesses of diffuser film to vary the amount of light that is transmitted through the standard in a controlled manner. An image of this calibration standard, which appears to a camera as a series of graduated stripes, with the darkest stripes corresponding to the thicker diffuser film layers and the lightest stripes corresponding to the thinner diffuser film layers. This image of the calibration standard can be acquired and flat-field corrected by the by the camera, and an intensity profile such as shown in FIG. 4 is extracted by computing the average gray-scale level within each section of the calibration pattern. The intensity profile of FIG. 4 shows an intensity level versus the number of layers of diffuser film in the standard for a selected light level.

One of the intensity profiles of FIG. 4 (extracted on an inspection system at some point in time) is designated as the baseline profile. Then, any other intensity profile, either from the same system at a different point in time or from a completely different system, can be mapped to this baseline profile through a simple linear projection. In other words, the baseline intensity profile is given by $I_B(L), L=1,2,\ldots,N$, wherein $N$ is the number of levels, and some other intensity profile, from a system to be calibrated, is given by $I(L), L=1,2,\ldots,N$, wherein $N$ is the number of levels.

Figure 5:
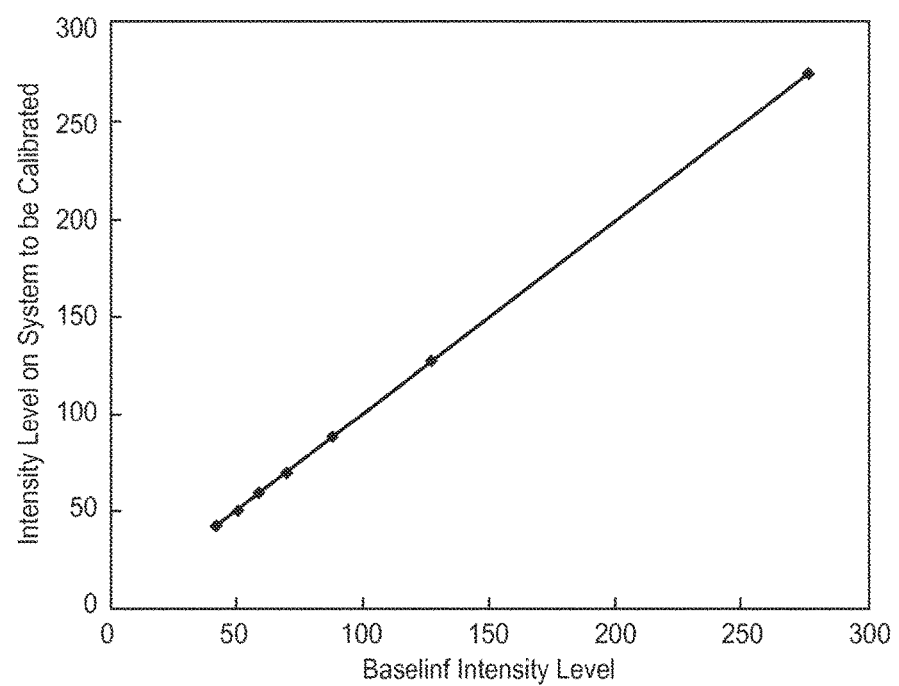
FIG. 5 is a plot of intensity level vs. baseline intensity level obtained for an optical data acquisition system.

Then we assume that there is a linear mapping from $I(L) \rightarrow I_g(L)$, parameterized by m and b, such that $I_B(L) = m\, I(L) + b.$ The linear mapping is acquired via a linear least-squares regression, as illustrated in the example of FIG. 5.

After the optional image calibration step 204, an image processing technique may be applied to measure the overall uniformity of an area of interest in a material at various size scales $s_1, s_2, \ldots, s_n$. Computation of uniformity across a range of sizes may capture some non-uniformities present at small size scales, while others are apparent only on larger size scales. Depending on the needs of a particular application, the uniformity at some size scales might be deemed as more important than at others. For example, in applications where a material is to be converted into small patches, a non-uniformity at a size scale much larger than these patches may not have any cosmetic or functional impact, since it will not be visible within the extend of and single small patch. On the other hand, larger-scale non-uniformities may cause differences in functional properties between samples. These are but two examples of the types of application-specific considerations that can be taken into account when choosing the range of size scales over which to estimate uniformity.

Referring again to FIG. 3, in step 206 a set of size scales at which to measure uniformity is initially defined based on, for example, the type of material being analyzed, the size of the final product, and the like. For example, for a given application, an operator might wish to characterize uniformity at scales between 25 mm and 100 mm, in increments of 25 mm. In some embodiments, the scales may be graduated, and the graduations may be equal, non-equal, or random.

In step 208 of FIG. 3, for each of the predefined size scales, the processor treats the image to remove and/or suppress the impact of non-uniformities that are much smaller than the size scale currently under consideration. This treatment step is referred to herein generally as low-pass filtering, and in some embodiments can suppress high frequencies in the image. In some embodiments, the low-pass filtering step performed by the process is equivalent to smoothing, but has theoretical interpretations in the frequency domain related to the Fourier Transform.

In some embodiments, the low pass filter is a "box filter," which consists of a two-dimensional kernel consisting of identical values. When convolved with an image, the box filter replaces each pixel in the size scale under consideration with the average of all neighboring pixel values. In other embodiments, a two-dimensional Gaussian kernel low-pass filter may be used, which can have more favorable characteristics in the frequency domain. When convolved with an image, the two-dimensional Gaussian kernel replaces each pixel with a weighted average of the intensities of the surrounding pixels, where the weights are given by the Gaussian kernel.

Regardless of the type of low-pass filter selected for a particular application, the algorithm suppresses high-frequency components of the image, which consist of image features much smaller than the size scale of interest. The low-pass filter allows measurement of only non-uniformities that are roughly near the size scale of interest, which removes the effect in a given patch caused by non-uniformities at much lower size scales. The smaller non-uniformities are captured at smaller size scales in the multiscale processing algorithms.

The application of a low-pass filter can be thought of in terms of how an observer visually perceives non-uniformities when physically looking at a sample. That is, when the observer stands close to the sample, very fine details of the surface are apparent, but not the overall uniformity on a large scale. On the other hand, when the observer stands far away from the sample, the overall uniformity and variations dominate the image, but the observer can no longer detect the fine level of detail that may exist at smaller size scales.

For example, in each iteration of the low-pass filtering algorithm described above, the low-pass filter can be selected to have a cutoff frequency equal to a predefined fraction of the current size scale at which to measure uniformity. In one specific example, if the size scale under consideration corresponds to 100 pixels, a box filter with a width of 20 pixels might be selected to suppress non-uniformities that are outside the size scale of interest.

Once the image is filtered to remove or reduce the impact of image features that are non-essential to the uniformity analysis at the selected size scale, in step 210 of FIG. 3 the image is divided into regions equal to the size scale of interest, referred to herein as patches. The image is divided into patches with a size equal to the current size scale of interest for measuring non-uniformities. A non-uniformity metric is subsequently computed on each patch, so this division has the effect of ensuring that information is not captured about non-uniformities at a larger size scale. Non-uniformities at finer size scales are suppressed through low-pass filtering in the previous step.

Referring to step 212 in FIG. 3, to calculate the non-uniformity of each patch, the processor applies a metric that characterizes the overall uniformity of the image of the patch in a quantitative and repeatable way. First, a small sub-image may be considered to be a function of two variables I(x,y), where x and y are indices of the pixel locations, and I(x,y) is the intensity of the pixel at location (x,y). Given this definition, simple statistical calculations can be used as a proxy for the uniformity (or (non-) uniformity) in the sub-image. For example, since in most cases a perfectly uniform patch is one in which all intensity values are equal, standard deviation of the patch is one straightforward choice for a metric. Given the patch I(x,y), the sample standard deviation can be computed as:

$$f_{std} = \frac{1}{N-1} \sum_x \sum_y (I(x,y) - \mu_I)^2,$$

where $\mu_{(I)}$ is the mean intensity in the patch, and N is the total number of pixels in it.

Other possible uniformity metrics include inter-quartile range (IQR), median absolute deviation (MAD), and the information entropy, among others. In some embodiments, the IQR, which is defined as the difference between the 75th and 25th percentile intensity values in the sample area, is more robust to outliers.

This uniformity analysis is computed for each patch using the metrics each time a new image is acquired by the camera 20 and the acquisition module 22 (FIG. 1). In some embodiments, in step 214 of FIG. 3, the processor in the analysis computer 24 can optionally perform further computations or analysis to aggregate the non-uniformity values in the patches. For example, in some embodiments, the uniformity values of the patches are aggregated to determine an overall uniformity value for the area of interest. In some non-limiting embodiments, for example, patch uniformity values can be aggregated using mean, median, standard deviation, and the like. In another example, the uniformity values of a selected array of patches within the area of interest can be aggregated to provide a uniformity value for the area of interest.

In step 215, the image processing steps 208, 210, 212, 214 are repeated for each size scale $s_1, s_2, \ldots, s_n$.

In some embodiments, as shown in step 216 of FIG. 3, the uniformity values can be displayed on the display 26 (FIG. 1) as plots of uniformity vs. size scale—this is convenient in cases where the processing is performed offline, since the goal in this setting can be to compare different materials or formulations. However, in cases where the image processing technique of this disclosure is meant to be used online for real-time inspection on a production line, it may be more beneficial to display plots of uniformity vs. time, showing separate curves for a few different size scales of interest. For online processing, this allows for visualization of changes in uniformity over time during a production run, or between runs, in a control-chart format.

The optical inspection system shown in FIGS. 1-2 may be used within a web manufacturing plant to apply the procedure of FIG. 3 for detecting the presence of non-uniformity defects in a web of a material. The inspection system may also provide output data that indicates a severity of each defect in real-time as the web is manufactured. For example, the computerized inspection systems may provide real-time feedback to users, such as process engineers, within web manufacturing plants regarding the presence of non-uniformities and their severity, thereby allowing the users to quickly respond to an emerging non-uniformity by adjusting process conditions to remedy a problem without significantly delaying production or producing large amounts of unusable material. The computerized inspection system may apply algorithms to compute the severity level by ultimately assigning a rating label for the non-uniformity (e.g., "good" or "bad") or by producing a measurement of non-uniformity severity of a given sample on a continuous scale or more accurately sampled scale.

The analysis computer 24 (FIG. 1) may store the feature dimension information for the web of material 12, including roll identifying information for the web and possibly position information for each measured area of interest 17, within a database 25. For example, the analysis computer 24 may utilize position data produced by a fiducial mark controller to determine the spatial position or image region of each measured feature within the coordinate system of the process line. That is, based on the position data from the fiducial mark controller, the analysis computer 24 determines the x, y, and possibly z position or range for each measured area of interest 17 within the coordinate system used by the current process line. For example, a coordinate system may be defined such that the x dimension represents a distance across the web, a y dimension represents a distance along a length of the web, and the z dimension represents a height of the web, which may be based on the number of coatings, materials or other layers previously applied to the web. Moreover, an origin for the x, y, z coordinate system may be defined at a physical location within the process line, and is typically associated with an initial feed placement of the web 12.

The database 25 may be implemented in any of a number of different forms including a data storage file or one or more database management systems (DBMS) executing on one or more database servers. The database management systems may be, for example, a relational (RDBMS), hierarchical (HDBMS), multidimensional (MDBMS), object oriented (ODBMS or OODBMS) or object relational (ORDBMS) database management system. As one example, the database 25 is implemented as a relational database available under the trade designation SQL Server from Microsoft Corporation, Redmond, Wash.

Once the process has ended, the analysis computer 24 may transmit the data collected in the database 25 to a conversion control system 60 via a network 50. For example, the analysis computer 24 may communicate the roll information as well as the uniformity information and respective sub-images for each uniformity measurement to the conversion control system 60 for subsequent, offline, detailed analysis. For example, the uniformity information may be communicated by way of database synchronization between the database 25 and the conversion control system 60.

In some embodiments, the conversion control system 60 may determine those products of products for which each anomaly may cause a defect, rather than the analysis computer 24. Once data for the finished web roll has been collected in the database 25, the data may be communicated to converting sites and/or used to mark anomalies on the web roll, either directly on the surface of the web with a removable or washable mark, or on a cover sheet that may be applied to the web before or during marking of anomalies on the web.

The components of the analysis computer 24 may be implemented, at least in part, as software instructions executed by one or more processors of the analysis computer 24, including one or more hardware microprocessors, digital signal processors (DSPs), application specific integrated circuits (ASICs), field programmable gate arrays (FPGAs), or any other equivalent integrated or discrete logic circuitry, as well as any combinations of such components. The software instructions may be stored within in a non-transitory computer readable medium, such as random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer-readable storage media.

Although shown for purposes of example as positioned within a manufacturing plant, the analysis computer 24 may be located external to the manufacturing plant, e.g., at a central location or at a converting site. For example, the analysis computer 24 may operate within the conversion control system 60. In another example, the described components execute on a single computing platform and may be integrated into the same software system.

The subject matter of the present disclosure will now be described with reference to the following non-limiting examples.

EXAMPLE

A dark field imaging system generally as depicted in FIGS. 1-2 was prepared and used to measure the uniformity of a non-woven web material in real-time, as it was being produced on a manufacturing line. Before performing the uniformity inspection, the imaging system was calibrated as described above. More specifically, the calibration pattern had 10 levels, ranging from 10% to 90% transmission. The calibration pattern was constructed using a film printed with fine lines ranging from 10 μm to 90 μm wide to modulate transmission. Layers of diffuser film commercially available as ILLUMINEX from General Electric of Fairfield, Conn., were also used. These layers were mounted together on a metallic frame.

The nonwoven web material was formed from polymeric strands using a conventional air-laid process, having a mean thickness of approximately 1.25 cm, but also having significant variations in thickness, including relatively thin and thick portions in close proximity.

The light source was placed approximately 10 cm below the surface of the web, and the camera was located approximately 102 cm above it. Dark-stripe illumination was used, as described in FIG. 2. In this case, the dark stripe was approximately 5 mm wide. The imaging optics were configured to achieve a crossweb resolution of 240 µm. A line scan camera commercially available as AVIIVA EM2 from E2V of Chelmsford, UK, was used together with a 40 mm focal length imaging lens. The light source was an LED-based line light commercially as COBRA SLIM from Pro Photonics of Salem, N.H. During the experimental run, the non-woven web was conveyed past the inspection system a line speed of 12.2 m/minute. An encoder wheel commercially available as DYNAPAR from Minarik Automation and Control of Eagan, Minn., was used to encode the translation of the web, such that electronic pulses were generated at a constant rate with respect to the web translation.

While the production line was running and the web was being conveyed, crossweb image lines at a fixed spacing along the downweb direction were acquired by the imaging system. These lines, when stacked together, formed a 2-dimensional image. These images were then processed according to the multi-scale uniformity algorithms described above.

Figure 6:
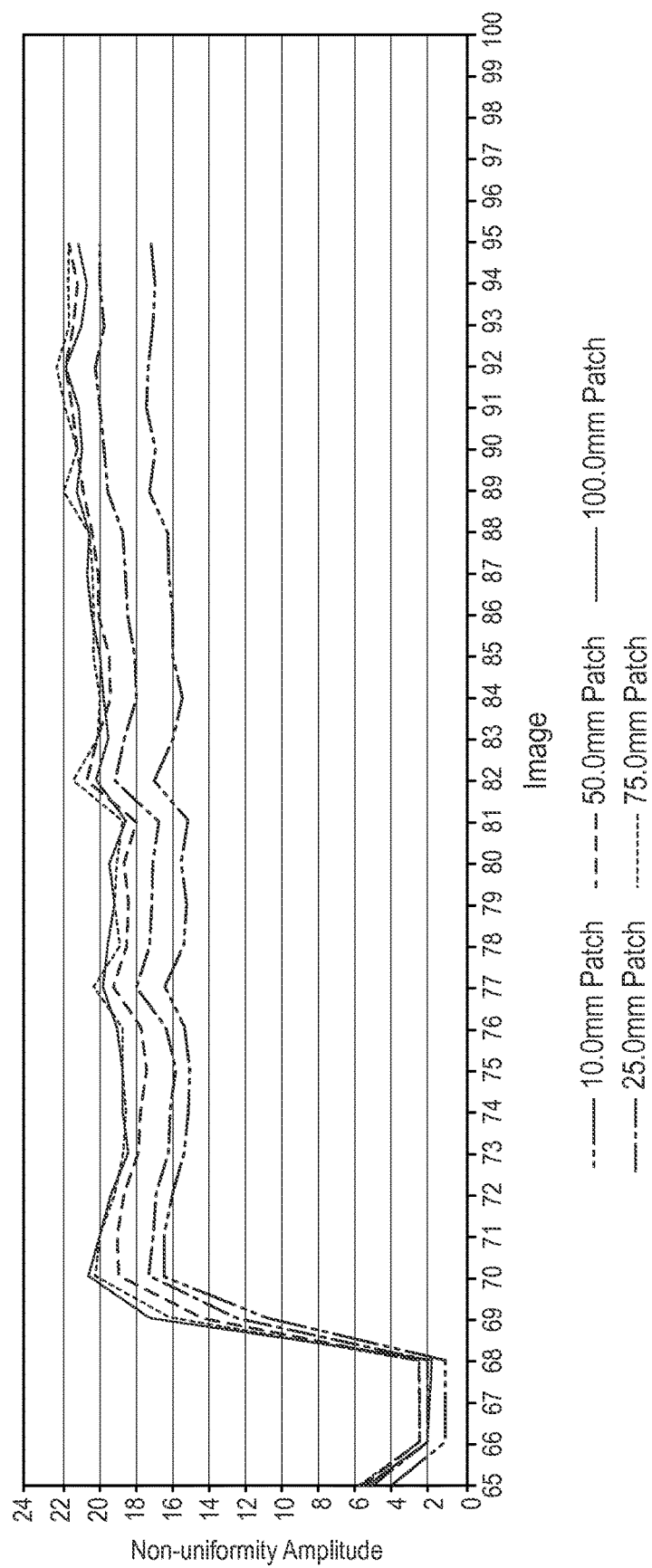
FIG. 6 is a plot of non-uniformity vs. time for varying patch sizes as obtained in the Example.

In this case, the non-uniformity was measured at 5 different size scales of interest. These were 10 mm, 25 mm, 50 mm, 75 mm, and 100 mm. For each image, a single metric of non-uniformity was computed at each size scale. These were displayed as a time-series plot, with non-uniformity vs. time displayed at each of the 5 size scales, resulting in 5 different curves on the plot. An example of a plot obtained in this manner is depicted in FIG. 6.

Various embodiments of the invention have been described. These and other embodiments are within the scope of the following claims.

The invention claimed is:

1. A method for characterizing the uniformity of a material, comprising:
    selecting a set of size scales at which to measure uniformity within an area of interest in an image of the material;
    suppressing features in the image smaller than a selected size scale of interest within the set of size scales;
    dividing the image into patches equal to the size scale of interest; and
    calculating a uniformity value within each patch.

2. The method of claim 1, wherein suppressing the features comprises processing the image with a low-pass filter, optionally wherein the low pass filter comprises a box filter with a cutoff frequency equal to a predetermined fraction of the size scale of interest, or a two-dimensional Gaussian kernel.

3. The method of claim 1, wherein the uniformity value is calculated by determining at least one of a standard deviation, an inter-quartile range (IQR), a median absolute deviation, or an information entropy of a selected characteristic of the patch.

4. The method of claim 3, wherein the selected characteristic of the patch comprises an intensity of light transmitted through the patch or reflected off a surface of the material comprising the patch.

5. The method of claim 1, further comprising at least one of calibrating the area of interest prior to removing the features, aggregating the uniformity values of the patches to determine a uniformity value for the area of interest, or aggregating the uniformity values of a selected array of patches within the area of interest to provide an uniformity value for the area of interest.

6. The method of claim 1, wherein the material is selected from wovens, non-wovens, paper, coatings, polymeric films and combinations thereof.

7. A method for characterizing the uniformity of a material, comprising:
    obtaining an image of an area of interest of the material by transmitting light through the material to an optical receiving device;
    selecting a graduated set of size scales at which to measure uniformity within the area of interest;
    convolving a low-pass filter with the image to suppress features in the image smaller than a selected size scale of interest within the graduated set of size scales;
    dividing the image into patches equal to the size scale of interest, wherein the patches each comprise an array of pixels; and
    determining a standard deviation of the light intensity in the pixels in the array to calculate a uniformity value within each patch.

8. The method of claim 7, wherein the low pass filter comprises a box filter with a width equal to a predetermined fraction of the pixels within the array, optionally wherein the low-pass filter replaces a selected pixel in the array with a weighted average of the light intensities of the pixels surrounding the selected pixel, and wherein the weighted average is determined by a two-dimensional Gaussian kernel.

9. The method of claim 7, further comprising at least one of determining an ideal pixel size for analyzing a selected non-uniformity, and scaling the area of interest to the ideal pixel size prior to removing the features; calibrating the area of interest prior to removing the features, or aggregating the uniformity values of the patches to determine a uniformity value for the area of interest.

10. An apparatus, comprising:
    at least one light source illuminating a web of a material;
    a camera that captures light transmitted through or reflected from an area of interest on the material to generate an image of the area of interest; and
    a processor which, in response to an input of a set of size scales at which to measure uniformity within the area of interest:
    convolves a low-pass filter with the image to suppress features in the image smaller than a selected size scale of interest within the set of size scales;
    divides the image into patches equal to the size scale of interest, wherein the patches each comprise an array of pixels; and
    calculates a uniformity value within each patch.

11. The apparatus of claim 10, wherein the processor calculates the uniformity value by determining at least one of a standard deviation, an inter-quartile range (IQR), a median absolute deviation, or an information entropy of a light intensity in the pixels in the array.

12. The apparatus of claim 10, wherein the processor calculates the uniformity value by determining the inter-quartile range (IQR).

13. The apparatus of claim 10, wherein the low pass filter comprises a box filter with a width equal to a predetermined fraction of the pixels within the array.

14. The apparatus of claim 10, wherein the low-pass filter replaces a selected pixel in the array with a weighted average of the light intensities of the pixels surrounding the selected pixel, and wherein the weighted average is determined by a two-dimensional Gaussian kernel.

15. The apparatus of claim 10, wherein the processor further determines an ideal pixel size for analyzing a selected non-uniformity in the material, and scales the area of interest to the ideal pixel size prior to removing the features.

16. The apparatus of claim 10, wherein the processor calibrates the area of interest prior to removing the features.

17. The apparatus of claim 10, wherein the processor aggregates the uniformity values of the patches to determine a uniformity value for the area of interest.

18. The apparatus of claim 10, wherein the processor aggregates the uniformity values of a selected array of patches within the area of interest to provide a uniformity value for the area of interest.

19. The apparatus of claim 10, wherein the material is selected from non-wovens and polymeric films.

20. The apparatus of claim 19, wherein the material is a non-woven.

21. The apparatus of claim 10, wherein the camera captures light transmitted through the area of interest.

22. The apparatus of claim 21, wherein only scattered light is captured by the camera to form the image.

23. The apparatus of claim 21, wherein a dark stripe is placed across the light source, and the camera is aimed directly at the dark stripe.

24. An online computerized inspection system for inspecting web material in real time, the system comprising:
at least one light source illuminating a web of a material;
a camera that captures light transmitted through or reflected from an area of interest on the material to generate an image of the area of interest; and
a computer executing software to characterize the uniformity of the material in the area of interest, wherein the computer comprises a processor which, in response to an input of a set of size scales at which to measure uniformity within the area of interest:
convolves a low-pass filter with the image to suppress features in the image smaller than a selected size scale of interest within the set of size scales;
divides the image into patches equal to the size scale of interest, wherein the patches each comprise an array of pixels; and
calculates a uniformity value within each patch.

25. The system of claim 24, further comprising a memory to store a web inspection model, wherein the computer executes software to compare the uniformity in the area of interest to the model and compute a severity of a non-uniformity defect in the material.

26. The system of claim 24, further comprising a user interface to output the severity of the defect to a user.

27. The system of claim 24, wherein the material is a non-woven.

* * * * *

UNITED STATES PATENT AND TRADEMARK OFFICE
CERTIFICATE OF CORRECTION

PATENT NO. : 9,841,383 B2  
APPLICATION NO. : 15/032735  
DATED : December 12, 2017  
INVENTOR(S) : Ribnick et al.

Page 1 of 1

It is certified that error appears in the above-identified patent and that said Letters Patent is hereby corrected as shown below:

On the Title Page

Page 2, Column 2  
Line 2, Delete "Universtiy" and insert -- University --, therefor.  
Line 4, Delete "www.dlic.mil" and insert -- www.dtic.mil --, therefor.  
Line 11, Delete "Zvvf" and insert -- Zwf --, therefor.  
Line 19, Delete "Co-OccuranceMatrizen" and insert -- Co-OccurrenceMatrizen --, therefor.  
Line 20, Delete "autmatisierten" and insert -- automatisierten --, therefor.  
Line 21, Delete "Miinchen" and insert -- Munchen --, therefor.

In the Drawings

Sheet 3 of 6 (Reference Numeral 214) (FIG. 3)  
Line 1, Delete "Aggrigate" and insert -- Aggregate --, therefor.

Sheet 5 of 6 (FIG. 5)  
Line 2 (X-axis), Delete "Baselinf" and insert -- Baseline --, therefor.

In the Specification

Column 5  
Line 35, Delete "means+/-five" and insert -- means +/-five --, therefor.

Column 7  
Line 59, After "112" insert -- . --.

Column 8  
Line 64 (Approx.), Delete "I(L)→I$_g$(L)," and insert -- I(L)→I$_B$(L), --, therefor.

Signed and Sealed this  
Tenth Day of July, 2018

Andrei Iancu  
*Director of the United States Patent and Trademark Office*